United States Patent [19]

Nerger et al.

[11] Patent Number: 4,973,414
[45] Date of Patent: Nov. 27, 1990

[54] POLYETHERS, PROCESS FOR THEIR PREPARATION AND LUBRICANTS CONTAINING THESE POLYETHERS

[75] Inventors: Dittmar Nerger; Karl-Heinz Hentschel, both of Krefeld; Christian Rasp, Bergisch Gladbach; Pramod Gupta, Bedburg; Siegfried Kussi, Leverkusen, all of Fed. Rep. of Germany

[73] Assignee: Bayer Aktiengesellschaft, Leverkusen, Fed. Rep. of Germany

[21] Appl. No.: 194,706

[22] Filed: May 17, 1988

[30] Foreign Application Priority Data

Jun. 2, 1987 [DE]  Fed. Rep. of Germany ....... 3718374

[51] Int. Cl.$^5$ ........................................... C10M 145/32
[52] U.S. Cl. .................... 252/52 A; 568/608
[58] Field of Search ...................... 252/52 A; 568/608

[56] References Cited

U.S. PATENT DOCUMENTS

| | | | |
|---|---|---|---|
| 3,933,662 | 1/1976 | Lowe | 252/52 A |
| 4,420,512 | 12/1983 | Ogawa et al. | 252/52 A |
| 4,521,326 | 6/1985 | Seibert et al. | 568/608 |
| 4,606,837 | 8/1986 | McEntire et al. | 568/608 |
| 4,774,017 | 9/1988 | Seibert et al. | 568/608 |
| 4,828,735 | 5/1989 | Minagawa et al. | 252/52 A |

FOREIGN PATENT DOCUMENTS 014696 1/1982 Japan .................. 252/52 A

Primary Examiner—Olik Chaudhuri
Assistant Examiner—Ellen McAvoy
Attorney, Agent, or Firm—Sprung Horn Kramer & Woods

[57] ABSTRACT

Monofunctional polyethers having hydroxyl groups contain as built-in terminal groups or monomers (a) 1 to 30% by weight of one or more $C_4$- to $C_{24}$-alkylmonophenols, (b) 1 to 30% by weight of one or more $C_8$- to $C_{24}$-monoalkanols, (c) 1 to 30% by weight of one or more $C_{10}$- to $C_{20}$-1,2-epoxyalkanes and (d) 45 to 80% by weight of propylene oxide or a lower alkylene oxide mixture consisting mainly of propylene oxide the sum of components (a) to (d) adding up to 100% by weight, and have average molecular weights of 600 to 2,500.

These polyethers are prepared by anionic epoxide polymerization and used as lubricants and components of lubricants.

7 Claims, 3 Drawing Sheets

POLYETHERS, PROCESS FOR THEIR PREPARATION AND LUBRICANTS CONTAINING THESE POLYETHERS

Aliphatic polyethers are in general hydrophilic substances which are soluble in water or can absorb water up to quite some percent by weight. Common polyethers are immiscible with hydrophobic substances. This is especially true for the vast majority of polyalkylene glycols which are used as lubricants. Thus, in Ullmanns Encyclopädie der technischen Chemie (Ullmann's Encyclopaedia of Industrial Chemistry), Verlag Chemie, Weinheim, 4th edition, volume 20, page 504, Table 29, for example, polyalkylene glycols are classified as being poorly miscible with mineral oils.

Nevertheless, attempts have already been made to develop special polyethers having good miscibility with mineral oils. Thus, Japanese Patent Application No. 50-133,205 (1975) describes polyethers based on ethylene oxide, propylene oxide and/or butylene oxide and a longer-chain 1,2-epoxyalkane with up to 26 C atoms having, if desired, one or two hydroxyl terminal groups. The publication discloses that, to guarantee miscibility with mineral oils, the 1,2-epoxyalkane having up to 26 C atoms must be present in the polyethers in an amount of approximately 40% by weight or more.

In contrast to ethylene oxide and propylene oxide, long-chain 1,2-epoxyalkanes are not petrochemical primary products, and must be prepared synthetically. The incorporation of large amounts of long-chain 1,2-epoxyalkanes into polyethers which are miscible with mineral oils is therefore technically and economically demanding and unsatisfactory.

Mineral oil-soluble polyethers are also described in EP-OS (European Published Specification) No. 0,064,236. These are tetrahydrofuran-containing copolyethers which are only accessible by a cationic polymerization process. Such cationic polymerization processes require special reactor materials and equipment due to the aggressive nature of the catalysts. Therefore they cannot be carried out in the plants which are customarily used for anionic epoxide polymerizations. In addition, to achieve good miscibilities with mineral oils, long-chain 1,2-epoxyalkanes in amounts of over 40% by weight are in practice necessary even for the polyethers described in EP-OS (European Published Specification) No. 0,064,236 (see Comparative Examples V to VIII and Table 2).

If an attempt is made to prepare low-viscous lubricants based exclusively on the polyethers known from EP-OS (European Published Specification) No. 0,064,236, for example, those of the important viscosity class ISO-VG 68, it is found that high evaporation losses occur (see Comparative Example 9) which can be repressed for only a short time by means of customary amounts of antioxidants. The addition of large amounts of antioxidants is not a solution of the problem, since it results in a deterioration of the lubricant properties.

Thus, hitherto there have been no mineral oil miscible polyethers which are technically and economically completely satisfactory in the field of lubricants.

There have now been found novel monofunctional polyethers having hydroxyl groups which are characterized in that they contain as built-in terminal groups or monomers (a) 1 to 30% by weight of one or more $C_4$- to $C_{24}$-alkylmonophenols, (b) 1 to 30% by weight of one or more $C_8$- to $C_{24}$-monoalkanols, (c) 1 to 30% by weight of one or more $C_{10}$- to $C_{20}$-1,2-epoxyalkanes and (d) 45 to 80% by weight of propylene oxide or a lower alkylene oxide mixture consisting predominantly of propylene oxide, the sum of components (a) to (d) adding up to 100% by weight, and in that they have average molecular weights of 600 to 2,500.

Preferably, the proportions of components (a) and (b) are each 5 to 15% by weight, the proportion of component (c) is 5 to 20% by weight, the proportion of component (d) is 50 to 65% by weight and the average molecular weight is 700 to 1,500. The molecular weight is preferably the weight average molecular weight as determined, for example, by GPC.

Suitable examples of component (a) are mono- or polyalkyl-substituted monophenols. In polyalkyl-substituted monophenols only one of the alkyl substituents must have between 4 and 24 C atoms. The alkyl substituent or, in the case of several alkyl substituents, the one with the longest carbon chain can be located in the o-, m- or p-position with respect to the phenolic OH group. Preferred are the m- and p-positions. Preferably all alkyl radicals present are saturated. However, unsaturated alkyl radicals may also be present, in particular those which do not have too much of an adverse effect on the stability of the polyether towards oxidation. Preferred monophenols contain alkyl substituents having 10 to 24 C atoms. Examples of component (a) are monoalkyl-substituted monophenols such as p-butylphenol, p-t-butylphenol, p-amylphenol, p-t-amylphenol, p-octylphenol, p-nonylphenol (it being possible for the nonyl radical to be derived for example from 1-nonene or from technical grade propylene trimers), p-dodecylphenol (it being possible for the dodecyl radical to be derived for example from 1-dodecene, from technical grade propylene tetramers or from technical grade isobutylene trimers), hexadecylphenols, octadecylphenols and monophenols derived from cashew-nut oil having an unsaturated or, for example due to hydrogenation, saturated aliphatic side chain in the m-position, dialkyl-substituted monophenols such as t-butylcresols, nonylcresols, dodecylcresols and dinonylphenols and trialkyl-substituted phenols such as 4-t-butyl-2,6-dimethylphenol. Dodecylphenols are particularly preferred as component (a).

Suitable examples of component (b) are straight-chain or branched, saturated or, if the stability of the polyethers towards oxidation is not too adversely affected, unsaturated aliphatic monoalcohols, each having 8 to 24 C atoms. Preferred examples are n-octanol, isooctanol, isononanol (for example in the form of an oxoalcohol based on diisobutene), decanols, dodecanols, isotridecanol (for example in the form of an oxoalcohol based on technical grade propylene tetramers), cetyl alcohol, stearyl alcohol, $C_{12}$- to $C_{20}$-oxoalcohols and $C_{16}$- to $C_{24}$-Guerbet alcohols (for example Relanit ® from Henkel, Düsseldorf). Particular preference is given to $C_{12}$- to $C_{18}$-alkanols such as isotridecanol and oxoalcohols having 12 to 18 C atoms.

Suitable examples of component (c) are 1,2-epoxydecane, 1,2-epoxydodecane, 1,2-epoxyhexadecane, 1,2-epoxyoctadecane, and also mixtures thereof. Component (c) can also comprise glycidyl ethers of straight-chain or branched $C_4$- to $C_{24}$-alkanols, such as 2-ethylhexyl-, octyl, decyl, isotridecyl, hexadecyl and octadecyl glycidyl ether. Preference is given to 1,2-epoxyalkanes.

If component (d) is made up of lower alkylene oxide mixtures consisting predominantly of propylene oxide, suitable examples of alkylene oxide mixtures are those which contain more than 60% by weight of propylene oxide and up to 40% by weight of $C_4$- to $C_6$-alkylene oxides. Preferably component (d) is propylene oxide.

The polyethers according to the invention are in general mixtures of various polyether monoalcohols with different terminal groups.

The polyethers according to the invention can be obtained for example by using the alkylmonophenols (component (a)) and the alkanols (component (b)) together as initiators for an anionic epoxide polymerization (epoxides=components (c) and (d)) in the same molar ratio which is also desired as the molar ratio of the monoether terminal groups in the polyether end product. An alternative procedure is to obtain the polyether end products having the specified molar ratio of monoether terminal groups by mixing together two or more such polyethers which each have different molar ratios of terminal groups. Thus, it is possible, for example, afterwards to mix together separately one polyether having an alkyl monoether terminal group and one having an alkylphenol monoether terminal group in the desired molar ratio of terminal groups. The method of preparation mentioned first is preferred.

In principle, it is also possible to achieve the incorporation of the alkylphenyloxy groups (component (a)) via alkylphenylglycidyl ethers as comonomers, for example by an anionic copolymerization of propylene oxide, long-chain 1,2-epoxyalkane (and/or alkyl-glycidyl ethers) and monomer mixtures containing alkylphenyl-glycidyl ethers in the presence of a $C_4$- to $C_{24}$-alkanol.

The incorporation of long-chain 1,2-alkylene oxide monomers (component (c)) relative to propylene oxide can be accomplished randomly, but also in blocks, and also by following a distribution gradient ("tapered copolymers"). In some instances, it may be advantageous to incorporate the alkylene oxide units of component (c) as a block at the hydroxyl terminus of the polyether monoalcohols. As a rule, a random incorporation is preferred.

The principles of performing an anionic epoxide polymerization are known to the expert (see for example Houben-Weyl, volume 14/2, page 425 et seq. (1963); Kirk-Othmer, volume 18, page 624 and 638 to 641 (1982) and Ullmann, Encyclopädie der technischen Chemie (Encyclopaedia of Industrial Chemistry), volume 19, pages 33 to 34 and 36 (1981)). During the preparation of the polyethers according to the invention care must be taken that volatile components and impurities are meticulously removed, for example by stripping, after-treatment in a thin-film evaporator or exhaustive distillation under a high vacuum up to high temperatures, for example to a maximum of 220° C. Otherwise, additional losses through evaporation which are not due to degradation or decomposition effects can occur when these compounds are used as lubricants.

The polyethers according to the invention are distinguished by the fact that they exhibit, even at low viscosities over a medium to long period, for example at temperatures in the range of 150° to 200° C. over a period of at least 6 months, small losses through evaporation and a high thermal and thermooxidative stability. Furthermore, they have the advantage of being accessible by a technically simple anionic polymerization process and of requiring smaller amounts of long-chain epoxides than in the past. The surprising fact is that these effects are obtained with polyethers having phenolic structural units, even though it is generally known that purely aliphatic structures supply particularly favourable properties for use as a lubricant (see for example Gunderson and Hart, Synthetic Lubricants, Reinhold Publ. Corp. New York, page 32 (1962) and Chemtech, December 1986, pages 752 to 755).

The polyethers according to the invention can, if desired after the addition of customary additives, be used as lubricants or lubricant components. The present invention therefore also relates to lubricants containing the polyethers according to the invention. Mixed with other polyethers, the polyethers according to the invention improve the thermooxidative stability thereof. By adding antioxidants, this stability is reinforced synergistically, as shown in detail in the examples. Finally, due to the specific solvent properties of the polyethers according to the invention together with mineral oils and/or poly-$\alpha$-olefins, partly or fully synthetic lubricants having a high performance profile can be formulated. Such mixtures preferably contain 50 to 95 parts by weight of a mineral oil fraction having lubricant viscosity or of a poly-$\alpha$-olefin, 5 to 50 parts by weight of the polyethers according to the invention and 0 to 10 parts by weight of conventional lubricant additives.

The term "lubricant viscosity" is to be understood as meaning a material property which excludes materials having a viscosity which is insufficient for lubricants. In general, a minimum viscosity (measured in a lubrication gap under a load) of at least 2 $mm^2/s$ is required.

Particular preference is given to those mixtures which contain 15 to 35 parts by weight of the polyethers according to the invention. Furthermore, it is also advantageous to mix the polyethers according to the invention with lubricants based on esters, phosphates, glycols and polyglycols, for example 5 to 50% by weight of the polyethers according to the invention with 50 to 95% by weight of lubricants based on other materials and, if desired, with conventional amounts of conventional additives.

Lubricants and lubricant mixtures containing the polyethers according to the invention can, in addition, contain conventional additives which improve the basic properties of lubricants, for example antioxidants, metal-passivating agents, rust inhibitors, viscosity index improvers, pour point depressants, dispersing agents, detergents, high-pressure additives and/or anti-wear additives.

The antioxidants can be for example phenol derivatives, in particular alkylated monophenols, alkylated hydroquinones, hydroxylated thiodiphenyl ethers, alkylidenebisphenols, benzylphenol compounds, acylaminophenols, esters or amides of $\beta$-(3,5-di-tert.-butyl-4-hydroxyphenyl)-propionic acid or esters of $\beta$-(5-tert.-butyl-4-hydroxy-3-methylphenyl)-propionic acid. All these phenol derivatives can contain alkyl groups. They can be for example methyl, ethyl, n-butyl, i-butyl, t-butyl, octyl, nonyl, dodecyl, octadecyl, cyclopentyl, cyclohexyl and methylcyclohexyl groups. If desired, even more substituents can be present, for example methoxy groups. Esters can be for example those with $C_1$- to $C_{20}$-mono- or polyalcohols, in particular esters of methanol, neopentylglycol and pentaerythritol. Amides can be for example those based on trimethylenediamine, hexamethylenediamine or hydrazine.

Typical representatives of said classes of phenol derivatives are for example 2,6-di-tert.-butyl-4-methylphenol, 2,6-di-tert.-butyl-4-methoxyphenol, 2,2'-thio-bis-(6-tert.-butyl-4-methylphenol), 2,2'-methylene-bis-(6-tert.-butyl-4-methylphenol), 2,2'-ethylidene-bis-(6-tert.-butyl-4-isobutylphenol), 1,3,5-tri-(3,5-di-tert.-butyl-4-hydroxybenzyl)-2,4,6-trimethylbenzene, bis-(4-tert.-butyl-3-hydroxy-2,6-dimethylbenzyl)-dithiol terephthalate, dioctadecyl 3,5-di-tert.-butyl-4-hydroxybenzyl phosphonate and 4-hydroxylauric anilide.

Antioxidants can also be amines, for example N,N'-diisopropyl-p-phenylenediamine, N-phenyl-1-naphthylamine, 4-butyrylamino-phenol, 2,4'-diaminodiphenylmethane or substituted diphenylamines.

Metal-passivating agents can be for example benzotriazole, tetrahydrobenzotriazole, 2-mercaptobenzothiazole, salicylidene-propylenediamine and salts of salicylaminoguanidines. Suitable rust inhibitors are for example organic acids, esters thereof, metal salts and anhydrides thereof, nitrogen-, phosphorus- and sulphur-containing compounds, such as N-oleoylsarcosin, lead naphthenate, dodecenylsuccinic anhydride, 4-nonylphenoxyacetic acid, oil-soluble alkylammonium carboxylates, substituted imidazolines and oxazolines, amino salts of the partial esters of phosphoric acid and barium dinonylnaphthalenesulphonates.

Viscosity index improvers are for example polymethacrylates, vinylpyrrolidone-methacrylate copolymers, polybutenes, olefin copolymers and styrene-acrylate copolymers, and also esters of aromatic dicarboxylic acids with polytetrahydrofurandiols (see DE-OS (German Published Specification) 3,221,137).

Suitable pour point depressants are for example polymethacrylates and alkylated naphthalene derivatives.

Examples of dispersing agents and/or surfactants are polybutenylsuccinimides, polybutenylphosphonic acid derivatives and basic magnesium, calcium and barium sulphonates and basic magnesium, calcium and barium phenolates.

High-pressure and/or wear-reducing additives can be for example compounds containing sulphur, phosphorus or halogens, such as sulphurized vegetable oils, zinc dialkyldithiophosphonates, tritolyl phosphate, chlorinated paraffins and alkyl and aryl disulphides.

Altogether, the additives are in general present in the lubricants which contain the polyethers according to the invention in an amount of no more than 10% by weight and individual additive components of no more than 3% by weight.

The examples which follow illustrate the present invention without limiting it thereto.

EXAMPLES

The properties of the products obtained by the following examples and comparative examples are apparent in particular from FIGS. 1 to 4 and Tables 1 and 2 with the pertinent explanations.

EXAMPLE 1

A mixture of 109.2 g of dodecylphenol (0.417 mol), 116.7 g of isotridecanol (0.584 mol) and 56 g of a 10% strength aqueous potassium hydroxide solution (0.1 mol) was dehydrated azeotropically using toluene, and the toluene was then removed by distillation. A 2 l autoclave was charged with the mixture thus obtained and heated to 170° C. with stirring. At this temperature, 533.6 g of propylene oxide (9.2 mol) were first metered in over 3 hours, and then 147.2 g of 1,2-epoxydodecane (0.8 mol) were metered in over 30 minutes. After the reaction had continued for 2 hours at 170° to 180° C., the mixture was cooled, the autoclave was emptied of its contents which were then neutralized by introducing carbon dioxide gas. Finally, the mixture was exhaustively distilled at 200° C. and 1 hPa and pressed through a sedimentation filter. The yield amounted to 834.0 g (about 92% of theory), the OH number of the product was 75.

EXAMPLE 2

A mixture of 104.8 g of dodecylphenol (0.4 mol), 80.0 g of isotridecanol (0.4 mol) and 45 g of a 10% strength aqueous potassium hydroxide solution (0.08 mol) was dehydrated azeotropically using toluene, and the toluene was then removed by distillation. A 2 l autoclave was charged with this mixture and the procedure was continued as described in Example 1, successively metering in 519.7 g of propylene oxide (8.96 mol) and 117.8 g of 1,2-epoxydodecane (0.64 mol). The yield amounted to 746.6 g (about 90.8% of theory), the OH number of the product was 66.

EXAMPLE 3

A mixture of 65.5 g of dodecylphenol (0.25 mol), 150.0 g of isotridecanol (0.75 mol) and 56 g of a 10% strength aqueous potassium hydroxide solution (0.1 mol) was dehydrated azeotropically using toluene, and the toluene was then removed by distillation. A 2 l autoclave was charged with this mixture, and the procedure was continued as described in Example 1. 533.6 g of propylene oxide (9.2 mol) and then 147.2 g of 1,2-epoxydodecane (0.8 mol) were added, the latter over 50 minutes. The yield amounted to 835.3 g (about 93.2% of theory), the OH number of the product was 74.

EXAMPLE 4

A mixture of 102.2 g of dodecylphenol (0.417 mol), 116.7 g of isotridecanol (0.584 mol) and 56 g of a 10% strength aqueous potassium hydroxide solution (0.1 mol) was dehydrated azeotropically using toluene, and the toluene was then removed by distillation. A 2 l autoclave was charged with this mixture, and the procedure was continued as described in Example 1. Over a period of 3 hours, a mixture of 556.8 g of propylene oxide (9.6 mol) and 73.6 g of 1,2-epoxydodecane (0.4 mol) was metered in. The yield amounted to 792 g (about 92.5% of theory), the OH number of the product was 75.

EXAMPLE 5

Example 4 was repeated, but 163.8 g of dodecylphenol (0.625 mol), 175.1 g of isotridecanol (0.876 mol), 84 g of a 10 % strength aqueous potassium hydroxide solution (0.15 mol), 800.4 g of propylene oxide (14.3 mol) and 220.8 g of 1,2-epoxydodecane (1.2 mol) were used. The yield amounted to 1279.9 g (about 94.1 % of theory), the OH number of the product was 67.

EXAMPLE 6

0.9 g of sodium were dissolved in 704 g of the polyether which had been obtained according to comparative Example 1. After heating this mixture to 150° C., 88.3 g of 1,2-epoxydodecane were added dropwise under nitrogen over 30 minutes and stirring was continued for 3 hours at 150° C. After cooling, the mixture was neutralized with 19.1 g of a 10% strength sulphuric acid and exhaustively distilled at 200° C. and 1 hPa and pressed through a sedimentation filter. The OH number of the product thus obtained was 59, the yield amounted to 739.2 g (about 93.3 % of theory).

EXAMPLE 7

The procedure of Example 6 was repeated with the exception that 44.2 g of 1,2-epoxydodecane were used. The OH number of the product was in this case 61, the yield amounted to 708.4 g (about 94.7 % of theory).

EXAMPLE 8

2 g of sodium (0.087 mol) were dissolved in 170 g of isotridecanol (0.85 mol), this mixture was placed into a 2 l autoclave and heated up to 170° C. with stirring. Over a period of 3 hours 552.2 g of propylene oxide (9.52 mol) and then over 40 minutes 187.7 g of p-nonylphenol glycidyl ether (0.68 mol) were metered in, and the reaction was continued for another 2 hours at 180° C. After cooling, the autoclave was emptied of its contents. The reaction mixture was neutralized with 10% strength sulphuric acid in an amount equivalent to that of the sodium employed, and exhaustively distilled at 200° C. and 1 hPa and then pressed through a sedimentation filter. The yield amounted to 812.5 g (about 89.3% of theory), the OH number of the product was 79.

EXAMPLE 9

In an experimental set-up, 722.7 g of dodecylphenol, 772 g of isotridecanol and 66.7 g of 45% strength potassium hydroxide solution were mixed. Water was distilled off from this mixture, towards the end at a vacuum of 1 hPa and 110° C. Over a period of 10 hours 3531.1 g of propylene oxide and then over 1.5 hours 974.2 g of 1,2-epoxydodecane were added at 100° to 110° C. The mixture was subsequently neutralized by adding 2073 g of a 12.5% strength sulphuric acid. Water was then distilled off and, finally, the mixture was heated for 3 hours at 105° C. and 1 hPa and subsequently cooled under nitrogen. The OH number of the product thus obtained was 66, the yield amounted to 5860 g (about 97.7% of theory).

EXAMPLE 10

The product obtained according to Example 5 was mixed with equal parts by weight of the product obtained according to Comparative Example IV. The loss through evaporation of this mixture, determined according to German Standard Specification DIN 51,581 (Noack test) was 5.8%. This mass loss is significantly less than the value of 12.45% expected theoretically (arithmetic mean).

COMPARATIVE EXAMPLE I

The procedure of Example 9 was repeated with the exception that 4505.3 g of propylene oxide and no 1,2-epoxydodecane were added over a period of 14.5 hours. The product obtained had an OH number of 64. The yield amounted to 5790 g (about 96.5 % of theory).

Comparative Example II

A mixture of 109.3 g of dodecylphenol (0.417 mol), 116.6 g of isotridecanol (0.583 mol) and 56 g of a 10% strength aqueous potassium hydroxide solution (0.1 mol) was dehydrated azeotropically using toluene, and the toluene was then removed by distillation. This mixture was charged into a 2 l autoclave which was heated to 170° C. with stirring. At this temperature, 696 g of propylene oxide (12 mol) were added over 3 hours. After the reaction had continued for 2 hours at 170° to 180° C., the mixture was cooled, the autoclave was emptied and the reaction mixture was neutralized using an equivalent amount of 10% strength aqueous sulphuric acid. The mixture was then distilled up to 200° C. at 1 hPa and finally pressed through a sedimentation filter. 880.4 g of product were obtained (about 95.5% of theory) which had an OH number of 76.

COMPARATIVE EXAMPLE III

The procedure of Comparative Example II was repeated with the exception that 27.4 g of dodecylphenol (0.105 mol), 93.3 g of isotridecanol (0.467 mol), 6.7 g of solid potassium hydroxide powder (0.12 mol) and 649.6 g of propylene oxide (11.2 mol) were reacted and worked up. 729.5 g of product were obtained (about 94.7 % of theory). The OH number of the product was 83.

COMPARATIVE EXAMPLE IV

A mixture of 1015 g of "Alfol ® 12/18" (which is a mixture of fatty alcohols in the range $C_{12}$ to $C_{18}$, available from Condea-Chemie GmbH, Brunsbüttel, and has an average molecular weight of 211; i.e. 1015 g correspond to about 4.8 mol) and 53.3 g of a 45% strength aqueous potassium hydroxide solution (0.428 mol) were dehydrated azeotropically using toluene, and the toluene was then removed. This mixture was charged into a reactor which was heated at 100° to 110° C. with stirring. At this temperature, 4985 g of propylene oxide (85.95 mol) were added over a period of 23 hours. After cooling, the mixture was neutralized with an equivalent amount of 10% strength aqueous sulphuric acid followed by exhaustive distillation at 40° C. and 1 hPa. The product was then pressed through a sedimentation filter. The yield amounted to 5600 g (about 93% of theory), the OH number being 47.

EXPLANATION OF THE FIGURES

FIG. 1

Curve 1 was obtained using a polyether according to the invention which had been prepared according to Example 5. Curve 2 was obtained using a polyether which had been prepared according to Comparative Example IV. Curve 3 was obtained using a 1:1 mixture by weight of polyethers which had been prepared according to Example 5 and Comparative Example IV. Curve 4 represents the arithmetic mean of curves 1+2 determined by calculation. FIG. 1 shows that the polyether according to the invention suffers substantially lower weight losses than the comparison polyether (curves 1 and 2). In addition, it is apparent that a 1:1 mixture by weight of these polyethers suffers a slower weight loss than corresponds to the arithmetic mean of the weight losses of both components (curves 3 and 4). For example, a weight loss of 10% is observed each time in the case of the polyether according to the invention after 16.5 minutes, in the case of the comparison polyether after 3.8 minutes and in the case of the 1:1 mixture by weight of both after 7.6 minutes, while for the 1:1 mixture by weight the time interval calculated from the arithmetic mean of the times measured for the two components is 5 minutes for a 10% weight loss.

FIG. 2

Figure 1:
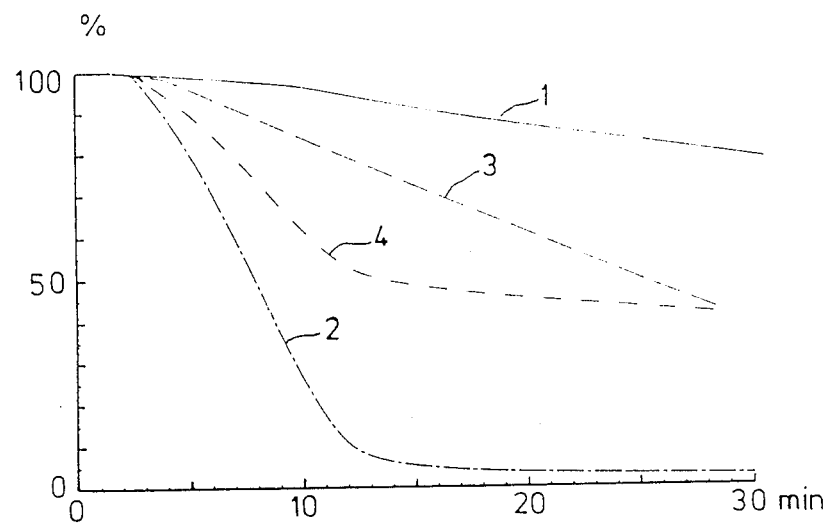
FIGS. 1 and 2 show the results of isothermogravimetric measurements performed with a thermobalance of the type TGS-2 (manufacturer: Perkin-Elmer and Co. GmbH, Überlingen/ Lake Constance) at 200° C. in air.

Curves 1 and 2 correspond to curves 1 and 2 from FIG. 1. Curve 3 was determined using a mixture of 99.5% by weight of the polyether according to the invention prepared according to Example 5 and 0.5% by weight of a commercial antioxidant mixture (2 parts of aralkylated diphenylamine and 1 part of 2,6-di-tert.-butyl-p-cresol), curve 4 was determined using a mixture of 99.5 % by weight of the polyether prepared according to Comparative Example IV and 0.5% by weight of the abovementioned commercial antioxidant mixture.

Figure 2:
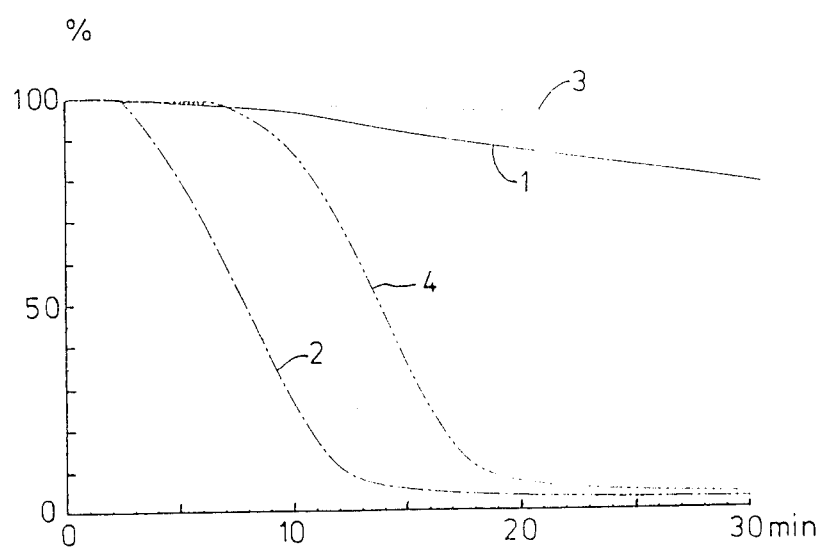

It is apparent from FIG. 2 that a conventional polyether (curve 2) suffers gradually slower weight losses by adding a conventional antioxidant mixture (curve 4), but still significantly faster than the polyether according to the invention without addition of antioxidant (curve 1) or even the polyether according to the invention with the addition of a conventional antioxidant mixture (curve 3). The polyether according to the invention mixed with a conventional antioxidant mixture shows an extremely slow weight loss.

For example, a weight loss of 5% is observed each time in the case of the polyether according to the invention with addition of antioxidant after 30 minutes, in the case of the polyether according to the invention without addition of antioxidant after 11.4 minutes, in the case of the comparison polyether with addition of antioxidant after 8.2 minutes and in the case of the comparison polyether without addition of antioxidant after 3.2 minutes.

Figure 3:
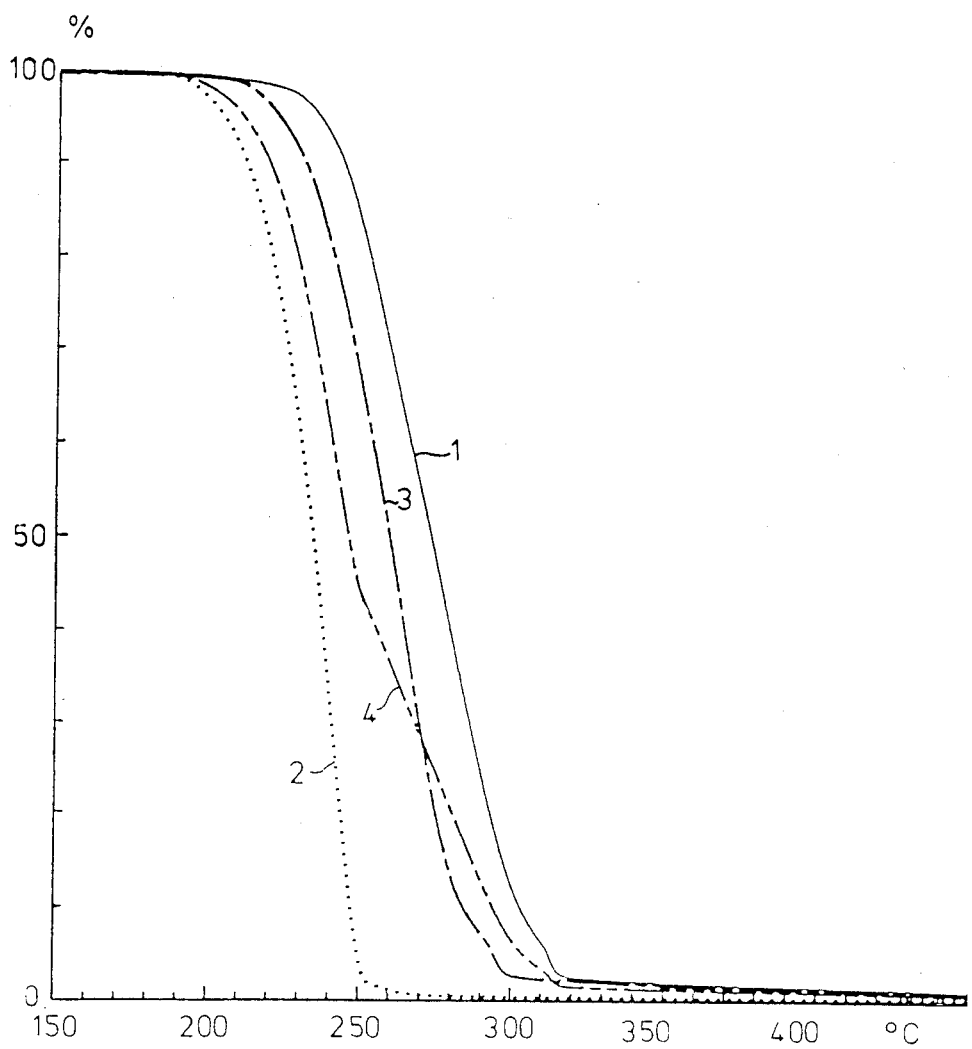
Figure 4:
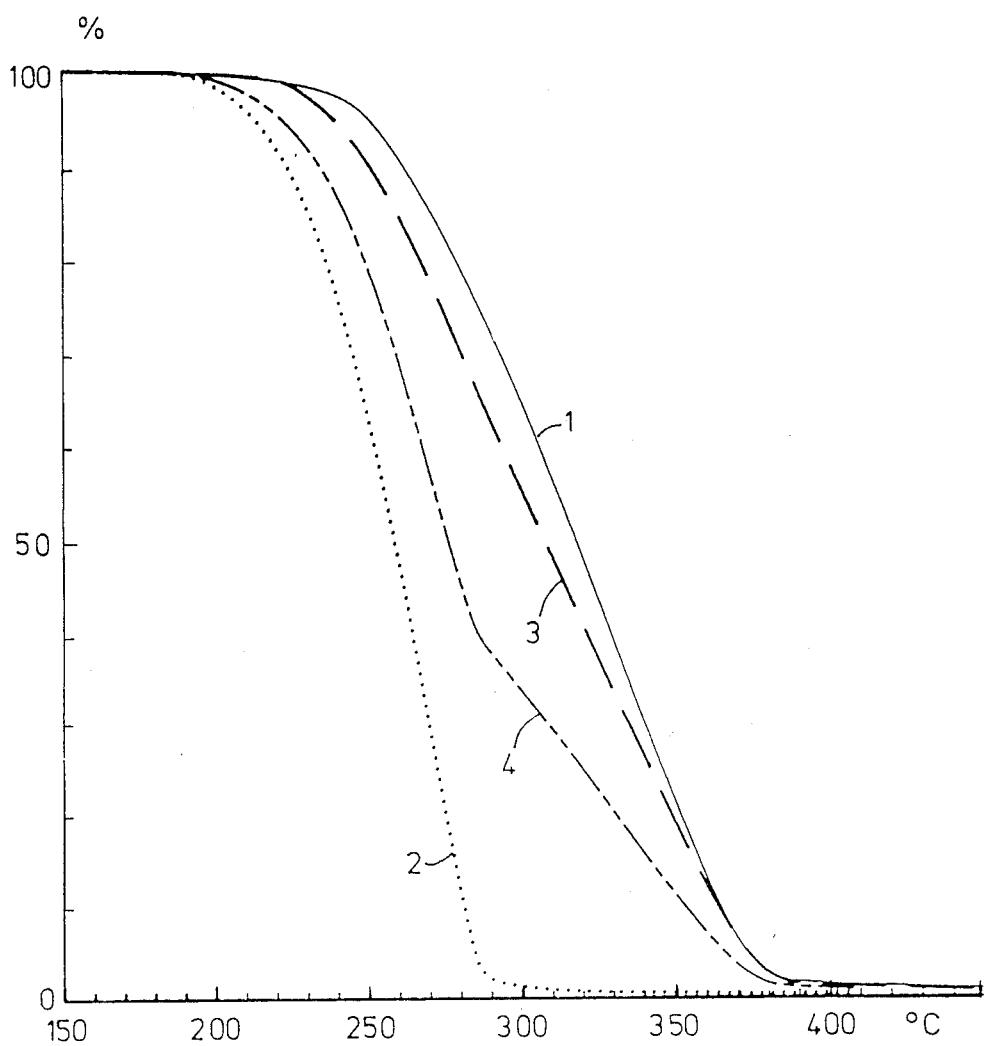

FIGS. 3 AND 4 Figures

FIGS. 3 and 4 show the results of dynamic thermogravimetric measurements performed with the same thermobalance (as described in FIGS. 1 and 2). The increase in temperature, in each case, was 20° C. per minute. In FIG. 3 measurements were done in air and in FIG. 4 in nitrogen.

In FIGS. 3 and 4, curve 1 was, in each case, determined using a polyether according to the invention which had been prepared according to Example 5. Curve 2 was, in each case, determined using a polyether which had been prepared according to Comparative Example IV. Curve 3 was, in each case, determined using a 1:1 mixture by weight of the polyethers which had been prepared according to Example 5 and Comparative Example IV. Curve 4 represents, in each case, the arithmetic mean of curves 1+2 determined by calculation.

From FIGS. 3 and 4, it is apparent that the polyether according to the invention (curve 1) is only degraded thermally at higher temperatures than the comparison polyether (curve 2). In addition, it is apparent that a 1:1 mixture by weight of these polyethers (curve 3) is degraded at higher temperatures than correspond to the arithmetic mean of both components (curve 4).

For example in air (FIG. 3), a weight loss of 5% is observed each time in the case of the polyether according to the invention at 230° C., in the case of the comparison polyether at 202° C. and in the case of the 1:1 mixture by weight of both at 220° C., whereas for the 1:1 mixture by weight a temperature of 215° C. is calculated for a 5% weight loss from the arithmetic mean of the temperatures measured for both components. The relationships among these four different temperatures are quite similar, if the measurements are done in nitrogen (FIG. 4). The corresponding values are then 240° C., 207° C., 232° C. and 213° C.

TABLE 1

|  | Example 1 | Comparative Example 1 | Example 5 | Comparative Example IV |
| --- | --- | --- | --- | --- |
| Viscosity at 40° C. [mm$^2$/s] | 65.8 | 66.7 | 68.5 | 58.6 |
| Viscosity at 100° C. [mm$^2$/s] | 9.7 | 10.1 | 10.3 | 11.2 |
| Pour point (°C.) | −37 | −35 | −40 | −37 |
| Viscosity index VIE | 129 | 136 | 136 | 192 |
| Loss through evaporation according to DIN 51,581 (% by weight) | 4.8 | 12.3 | 3.5 | 21.4 |
| Almen-Wieland test (values at the load limit) | | | | |
| Weld point (N) | 7000 | 7000 | 10000 | 7000 |
| Force of friction (N) | 920 | 1600 | 1100 | 1160 |
| Temperature (°C.) | 34 | 49 | 38 | 42 |
| Reichert frictional-wear test (at a load of 15 N) | | | | |
| Wear area (mm$^2$) | 12.9 | 12.3 | 11.7 | 12.5 |
| Specific load capacity (MPa) | 23.2 | 24.3 | 25.6 | 24 |
| Solubility in mineral oils (addition of 50% by volume) to paraffin-base | | | | |
| oil basis     clear until (°C.) | −14 | −13 | −16 | −10 |
| to mixed-base oil basis     clear until (°C.) | −10 | −10 | −13 | +1 |
| to naphthene-base oil basis     clear until (°C.) | <−60 | −49 | <−60 | −35 |
| to poly-α-olefin oil basis     clear until (°C.) | <−60 | −4 | <−60 | −10 |

Explanations regarding Table 1

In Examples 2 to 4 and 6 to 9 and Comparative Examples II and III, the following losses through evaporation were measured:
Example 2: 2.9
Example 3: 2.9
Example 4: 5.2
Example 6: 7.0

Example 7: 8.8
Example 8: 9.5
Example 9: 4.6
Comparative Example II: 12.2
Comparative Example III: 12.3

In the products of Examples 2 to 4 and 6 to 9 and of Comparative Examples II and III, the remaining measurements do not show any significant deviations compared to the corresponding measurements of the products of Example 1 and Comparative Example I (exception Examples 6 to 8, solubility in poly-α-olefins).

It is apparent that the strongly improved loss through evaporation of the polyethers according to the invention does not have any adverse effect on the lubricating properties and the solubility in mineral oils (exception see above).

The pure mineral oils had the cloud points given in Table 2.

Comparative Examples V to VIII

The miscibilities of polyethers with mineral oils were determined according to EP-OS (European Published Specification) No. 0,064,236 having been prepared as follows: Propylene oxide (PO), dodecene oxide (DO) and alcohol were added dropwise to a mixture of tetrahydrofuran (THF), alcohol and boron trifluoride-tetrahydrofuranate ($BF_3$-T) at 55° C. over a period of 2 to 6 hours. The reaction was continued for 1 to 2 hours, then neutralized with sodium carbonate (S), and the mixture was distilled exhaustively in vacuo up to 200° C. at 1 hPa and pressed through a sedimentation filter.

Comparative Example V

Amounts:
234.4 g of THF,
0.45 g of methanol,
30 g of $BF_3$-T;
1492.9 g of PO,
685.5 g of DO,
8 g of methanol;
38 g of S.

Product: OH number: 110, dodecene oxide content: 28.1%.

Comparative Example VI

Amounts:
208.8 g of THF,
0.4 g of methanol,
26.7 g of $BF_3$-T;
1262.1 g of PO,
832.4 g of DO,
7.1 g of methanol;
33 g of S.

Product: OH number: 95, dodecene oxide content: 35.6%.

Comparative Example VII

Amounts:
247.5 g of THF,
2.3 g of butane-1,4-diol,
8.5 g of $BF_3$-T;
523.0 g of PO,
758.4 g of dodecene oxide,
44.5 g of butane-1,4-diol together with 302.1 g of THF;
12.3 g of S.

Product: OH number: 51, dodecene oxide content: 40.1%.

Comparative Example VIII

Amounts:
382.5 g of THF;
31.7 g of methanol,
13.8 g of $BF_3$-T;
79.8 g of PO,
712 g of DO together with 409.5 g of THF;
17.7 g of S.

Product: OH number: 45, dodecene oxide content: 43.4%.

The polyethers thus prepared were in each case mixed with various mineral oils in a ratio of 1:1 by volume. The clear point of the pure mineral oils and the mineral oil/polyether mixtures were determined according to DIN 51,597. The results are listed in Table 2.

TABLE 2

| Type of mineral oil | without additive | Clear points [°C.] with addition of polyether from Comparative Example | | | |
|---|---|---|---|---|---|
| | | V | VI | VII | VIII |
| White oil 68 | −18 | >+25 | +15 | +10 | −15 |
| Compressor oil 100 | −8 | >+25 | >+25 | ±0 | −19 |
| Refrigerator oil C/68 | <−60 | +15 | −22 | −45 | <−60 |
| Hitec E 168 | <−60 | +10 | −25 | −35 | <−60 |

Explanation Regarding Table 2

Low clear points signify good miscibility with mineral oils. It can be seen that about the same or lower clear points, compared to the respective pure mineral oil, occur only after addition of a polyether which contains more than 40% by weight of dodecene oxide (Comparative Example VIII).

Comparative Example IX

According to EP-OS (European Published Specification) No. 0,064,236, a polyether having a lower and a higher viscosity were prepared and the viscosities and losses through evaporation (Noack test according to German Standard Specification (DIN 51, 581) thereof were determined.

(a) A polyether initiated with isotridecanol had a viscosity of 96.7 mm²/s and a loss through evaporation of 17.5% by weight at 40° C.

(b) A polyether initiated with the corresponding molar amount of butane-1,4-diol (instead of isotridecanol) and prepared in all other respects identically to (a) had a viscosity of 240 mm²/s and a loss through evaporation of 9.5% by weight at 40° C.

It is apparent that low-viscous polyethers according to EP-OS (European Published Specification) No. 0,064,236 have a high loss through evaporation.

Comparative Example X

Using two lubricants which correspond to the state of the art, parameters which relate to industrial application were determined.

Comparative Example Xa 455.3 g of propylene glycol were mixed with 66.7 g of 45% strength aqueous potassium hydroxide solution followed by removal of water from this mixture by heating to 110° C. at a pressure of 1 hPa. Over a period of 6 hours 5544.7 g of propylene oxide were then added at 105° C., and the mixture was then neutralized by adding 218.3 g of 12% strength sulphuric acid and 600 g of water. Water was distilled off, and heating was continued for 3 hours at 105° C. at a pressure of 1 hPa, and the mixture was cooled under nitrogen and pressed through a sedimentation filter. 5800 g of a product with an OH number of 112 were obtained. The product corresponds to DE-AS (German Published Specification) No. 1,130,176.

Comparative Example Xb

Commercial mineral oil, type HL-oil compressor oil 68.

The results of the measurements are shown in Table 3.

TABLE 3

|  | Comparative Example Xa | Comparative Example Xb |
|---|---|---|
| Viscosity at 40° C. [mm²/s] | 68 | 70.9 |
| Viscosity at 100° C. [mm²/s] | 11 | 8.9 |
| Pour point (°C.) | −42 | −19 |
| Viscosity index VIE | 150 | 98.0 |
| Loss through evaporation according to DIN 51,581 (% by weight) | 21.7 | 5.0 |
| Almen-Wieland test (values at the load limit) | | |
| Weld point (N) | 10000 | 1500 |
| Force of friction (N) | 2700 | 300 |
| Temperature (°C.) | 94 | 24 |
| Reichert frictional-wear test (at a load of 15 N) | | |
| Wear area (mm²) | 11.6 | 26.3 |
| Specific load capacity (MPa) | 25.8 | 11.4 |
| Solubility in mineral oils (addition of 50% by volume) to paraffin-base | | |
| oil basis clear until (°C.) to mixed-base | >+20 | −17 |
| oil basis clear until (°C.) to naphthene-base | >+20 | −14 |
| oil basis clear until (°C.) to poly-α-olefin | >+20 | −27 |
| oil basis clear until (°C.) | >+20 | −16 |

Explanations regarding Table 3

It is apparent that the polyether lubricant oil according to DE-AS (German Published Specification) No. 1,130,176 (see Comparative Example Xa) represents, at a given viscosity, a combination of bad loss through evaporation, good Almen-Wieland and Reichert tests and a non-existent miscibility with mineral oils, whereas the commercial mineral oil (see Comparative Example Xb) represents, at a given viscosity, a combination of acceptable loss through evaporation, poor Almen-Wieland and Reichert tests and acceptable miscibility with mineral oils. In contrast, polyethers according to the invention (see Table 1, Examples 1 and 5), are distinguished by good values in all parameters which relate to industrial application, i.e. they show, at a given viscosity, a combination of a small loss through evaporation and good Almen-Wieland and Reichert tests and also good miscibility with mineral oils.

What is claimed is:

1. A hydroxyl group containing monofunctional polyether which contains as built-in terminal groups or monomers
   (a) 1 to 30% by weight of one or more $C_4$- to $C_{24}$-alkylmonophenols,
   (b) 1 to 30% by weight of one or more $C_8$- to $C_{24}$-monoalkanols,
   (c) 1 to 30 % by weight of one or more $C_{10}$- to $C_{20}$-1,2-epoxyalkanes and
   (d) 45 to 80 % by weight of alkylene oxide selected from the group consisting of propylene oxide and lower alkylene oxide mixtures containing mainly propylene oxide,
   in which the sum of components (a) to (d) adds up to 100% by weight,
   and which has an average molecular weight in the range of 600 to 2,500.

2. A polyether according to claim 1, in which the proportions of components (a) and (b) are each 5 to 15% by weight, the proportion of component (c) is 5 to 20% by weight, the proportion of component (d) is 50 to 65% by weight and which has an average molecular weight in the range of 700 to 1,500.

3. A polyether according to claim 1, in which in component (a) the alkyl substituent or, in the case of a plurality of alkyl substituents, the one with the longest carbon chain, is located in the m- or p-position relative to the phenolic OH group, in which component (b) is selected from the group consisting of n-octanol, isooctanol, isononanol, decanols, dodecanols, isotridecanol, cetyl alcohol, stearyl alcohol, $C_{12}$- to $C_{20}$-oxoalcohols and $C_{16}$- to $C_{24}$- Guerbet alcohols, in which component (c) is selected from the group consisting of 1,2-epoxydecane, 1,2-epoxydodecane, 1,2-epoxyhexadecane, 1,2-epoxyoctadecane and mixtures thereof and in which component d) is propylene oxide.

4. A process for preparing a hydroxyl group containing monofunctional polyether which contains as built-in terminal groups or monomers
   (a) 1 to 30% by weight of one or more $C_4$- to $C_{24}$-alkylmonophenols,
   (b) 1 to 30% by weight of one or more $C_8$- to $C_{24}$-monoalkanols,
   (c) 1 to 30% by weight of one or more $C_{10}$- to $C_{20}$-1,2-epoxyalkanes and
   (d) 45 to 80 % by weight of alkylene oxide selected from the group consisting of propylene oxide and lower alkylene oxide mixture containing mainly of propylene oxide,
   in which the sum of components (a) to (d) adds up to 100% by weight,
   and which has an average molecular weight in the range of 600 to 2,500,
   in which component (a) and component (b) are used together as initiators for an anionic epoxide polymerization with the epoxides corresponding to components (c) and (d) in the same molar ratio which is also desired as the molar ratio of the monoether terminal groups in the polyether end product.

5. The process according to claim 4, in which volatile components and impurities are removed by stripping, after-treatment in a thin-film evaporator or exhaustive distillation under a high vacuum.

6. A lubricant, which contains a polyether according to claim 1.

7. A lubricant according to claim 6, which additionally contains components selected from the group consisting of additives, other polyethers than those according to claim 1, mineral oils, poly-α-olefins and lubricants based on esters, phosphates, glycols and/or polyglycols.

* * * * *